United States Patent
Gartner et al.

(10) Patent No.: US 10,512,465 B2
(45) Date of Patent: Dec. 24, 2019

(54) METHOD AND APPARATUS FOR COUPLING LEFT VENTRICLE OF THE HEART TO THE ANTERIOR INTERVENTRICULAR VEIN TO STIMULATE COLLATERAL DEVELOPMENT IN ISCHEMIC REGIONS

(71) Applicant: Ension, Inc., Pittsburgh, PA (US)

(72) Inventors: Mark J Gartner, Pittsburgh, PA (US);
Patrick Cahalan, Cape Coral, FL (US);
Linda Cahalan, Cape Coral, FL (US)

(73) Assignee: ENSION, INC., Butler, PA (US)

( * ) Notice: Subject to any disclaimer, the term of this patent is extended or adjusted under 35 U.S.C. 154(b) by 348 days.

(21) Appl. No.: 15/450,327

(22) Filed: Mar. 6, 2017

(65) Prior Publication Data

US 2017/0182308 A1   Jun. 29, 2017

Related U.S. Application Data

(62) Division of application No. 14/452,403, filed on Aug. 5, 2014, now Pat. No. 9,585,665.
(Continued)

(51) Int. Cl.
*A61B 17/11* (2006.01)
*A61B 17/00* (2006.01)
(Continued)

(52) U.S. Cl.
CPC ........ *A61B 17/11* (2013.01); *A61B 17/00234* (2013.01); *A61B 2017/00252* (2013.01);
(Continued)

(58) Field of Classification Search
CPC .............. A61B 17/00234; A61B 17/11; A61B 2017/00252; A61B 2017/1107;
(Continued)

(56) References Cited

U.S. PATENT DOCUMENTS 5,033,998 A   7/1991 Corday
7,798,953 B1   9/2010 Wilk
(Continued)

OTHER PUBLICATIONS

Pratt FH., The nutrition of the heart through the vessels of Thebesian and the coronary veins. Am J Physiol 1: 86-103, 1898, proposed the idea of perfusion of the heart muscle through the coronary sinus in isolated feline hearts.
(Continued)

*Primary Examiner* — Katherine M Shi
(74) *Attorney, Agent, or Firm* — Blynn L. Shideler; Krisanne Shideler; BLK Law Group

(57) ABSTRACT

An apparatus for stimulation of collateral development in ischemic cardiac regions comprises a mechanism for fluid coupling of the left ventricle of the heart to the anterior interventricular vein to stimulate collateral development in ischemic regions. The fluid coupling of the left ventricle of the heart to the anterior interventricular vein includes a control of the diastolic/systolic pressure in the venous system to be within about 20-50 mmHg. The fluid coupling of the left ventricle of the heart to the anterior interventricular vein includes inserting a transmyocardial conduit into the left ventricle and a tri-directional coupler attached to the anterior interventricular vein. An associated method for stimulation of collateral development in ischemic cardiac regions via the fluid coupling of the left ventricle of the heart to the anterior interventricular vein is disclosed.

6 Claims, 2 Drawing Sheets

Related U.S. Application Data

(60) Provisional application No. 61/862,155, filed on Aug. 5, 2013.

(51) Int. Cl.
  *A61F 2/06* (2013.01)
  *A61B 18/00* (2006.01)

(52) U.S. Cl.
  CPC .......... *A61B 2017/1107* (2013.01); *A61B 2017/1135* (2013.01); *A61B 2018/00053* (2013.01); *A61F 2/064* (2013.01)

(58) Field of Classification Search
  CPC ........ A61B 2017/1135; A61B 17/0206; A61B 2017/00243; A61F 2/064; A61F 2/2493
  USPC .......................................................... 606/53
  See application file for complete search history.

(56) References Cited

U.S. PATENT DOCUMENTS

| | | | |
|---|---|---|---|
| 9,585,665 | B2 | 3/2017 | Gartner et al. |
| 2002/0123786 | A1 | 9/2002 | Gittings |
| 2003/0229365 | A1* | 12/2003 | Whayne .............. A61B 17/064 606/153 |
| 2005/0149093 | A1* | 7/2005 | Pokorney ........... A61B 17/3415 606/185 |
| 2011/0118763 | A1* | 5/2011 | Beane ................. A61B 17/11 606/153 |

OTHER PUBLICATIONS

Syeda B, Schukro C, Heinze G, Modaressi K, Glogar D, Maurer G, Mohl W. The salvage potential of coronary sinus interventions: meta-analysis and pathophysiologic consequences. J Thorac Cardiovasc Surg 127: 1703-1712, 2004.

Zalewski A, Goldberg S, Slysh S, Maroko PR. Myocardial protection via coronary sinus interventions: superior effects of arterialization compared with intermittent occlusion. Circulation 71: 1215-1223, 1985.

Oesterle SN, Reifart N, Hauptmann E, Hayase M, Yeung AC. Percutaneous in situ coronary venous arterialization. Report of the first human catheter-based coronary artery bypass. Circulation 103: 2539-2543, 2001.

Raake P, Hinkel 1 R, Kupatt C, Von Brühl ML, Beller S, Andrees M, Vicol C, Boekstegers P. Percutaneous approach to a stent-based ventricle to coronary vein bypass (venous VPASS): comparison to catheter-based selective pressure-regulated retro-infusion of the coronary vein. Eur Heart J 26: 1228-1234, 2005.

Ghassan S. Kassab, Jose A. Navia, Keith March and Jenny Susana Choy, Coronary venous retroperfusion: an old concept, a new approach, J Appl Physiol 104:1266-1272, 2008. First published Feb. 21, 2008; doi: 10.1152/japplphysiol.00063.2008.

Motoya Hayase, MD, Yoshiaki Kawase, MD, Ryuichi Yoneyama, MD, Kozo Hoshino, MD, Jennifer McGregor,1 Briain D. MacNeill, MD, Harry C. Lowe, MD, PHD, Daniel Burkhoff, MD, PHD, Peter Boekstegers, MD, and Roger J. Hajjar1, MD, Catheter-Based Ventricle-Coronary Vein Bypass, Catheterization and Cardiovascular Interventions 65:394-404 (2005).

* cited by examiner

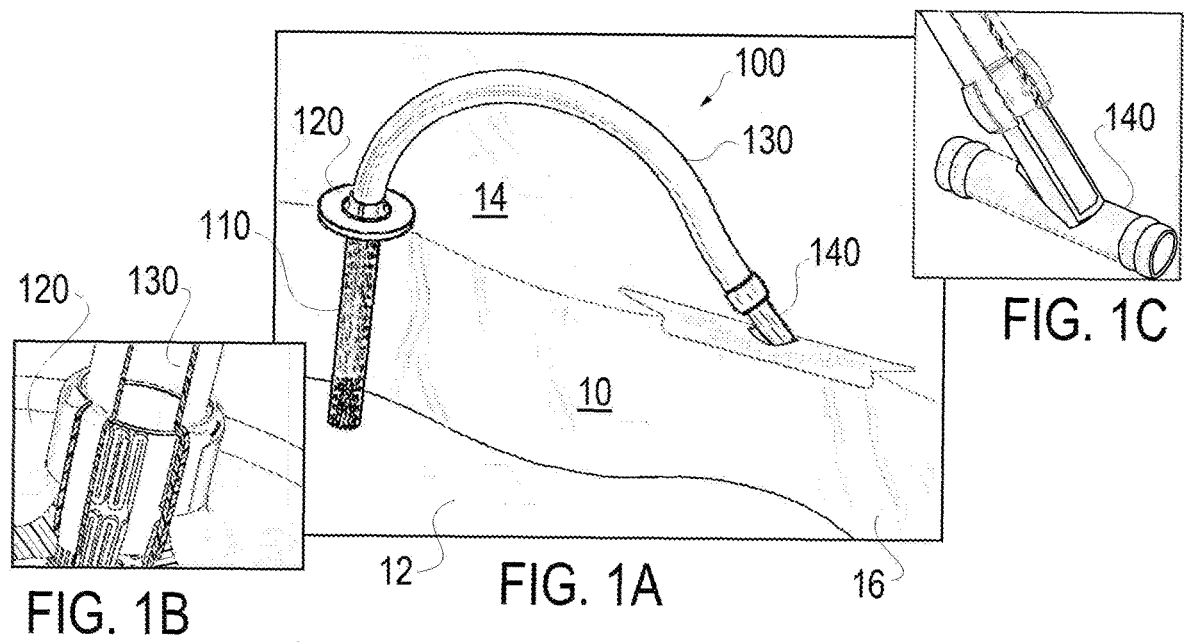
FIG. 1B  FIG. 1A  FIG. 1C
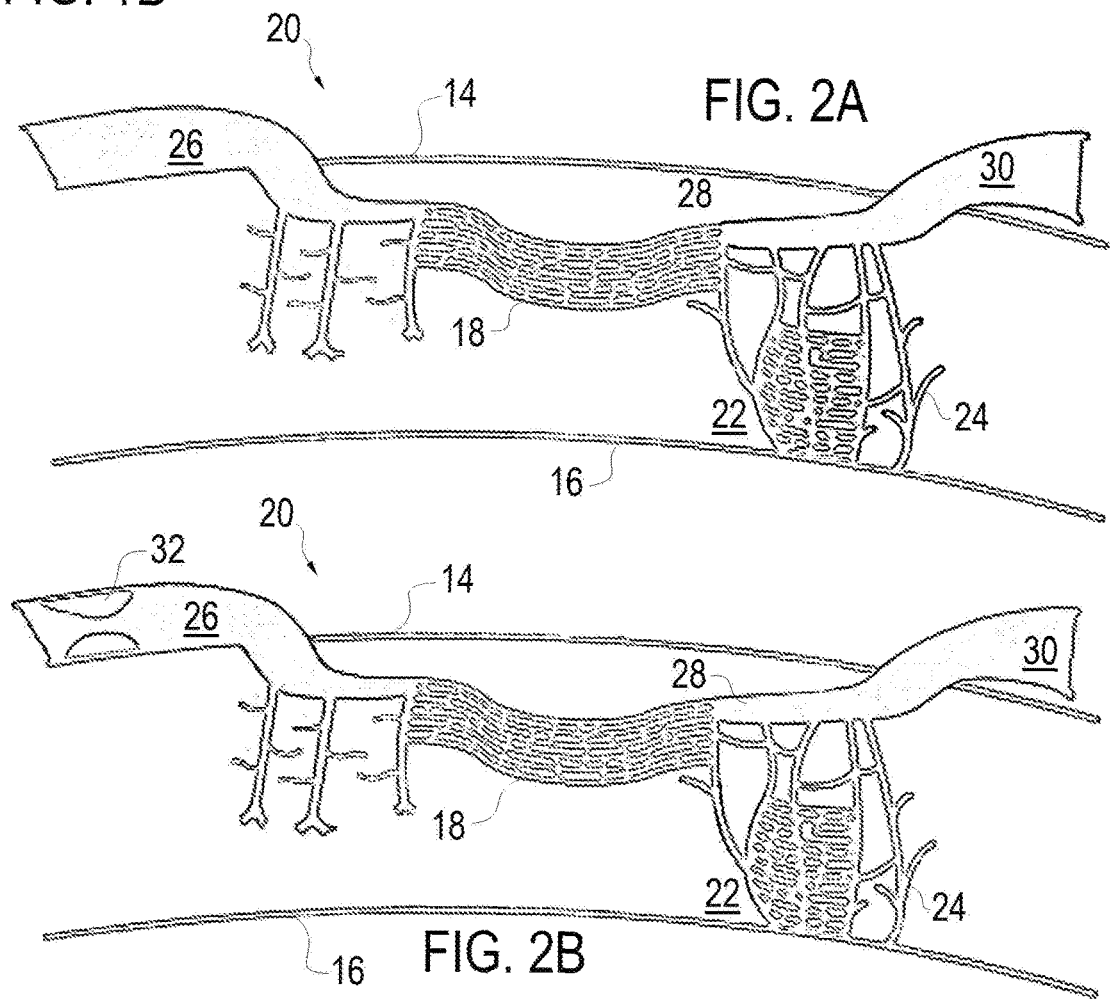
FIG. 2A
FIG. 2B

METHOD AND APPARATUS FOR COUPLING LEFT VENTRICLE OF THE HEART TO THE ANTERIOR INTERVENTRICULAR VEIN TO STIMULATE COLLATERAL DEVELOPMENT IN ISCHEMIC REGIONS

RELATED APPLICATIONS

The present application is a divisional application of U.S. patent application Ser. No. 14/452,403 filed Aug. 5, 2014 and published as publication number 2015-0038999 on Feb. 5, 2015 and issued Mar. 7, 2017 as U.S. Pat. No. 9,585,665, which published patent application is incorporated herein by reference. U.S. patent application Ser. No. 14/452,403 claims the benefit of U.S. Provisional Patent Application Ser. No. 61/862,155 entitled "Method and Apparatus for Coupling Left Ventricle of the Heart to the Anterior Interventricular Vein to Stimulate Collateral Development in Ischemic Regions" filed on Aug. 5, 2013.

BACKGROUND OF THE INVENTION

1. Field of the Invention

The present invention relates to stimulation of collateral development in ischemic cardiac regions, more specifically to an apparatus for coupling left ventricle of the heart to the anterior interventricular vein to stimulate collateral development in ischemic regions.

2. Background Information

Heart disease is the leading cause of death for both men and women. According to the Center for Disease Control and Prevention, every year, about 720,000 Americans have a heart attack. Approximately 600,000 people die from cardiovascular disease (CVD) in the United States each year (about 1 out of every 4 deaths) with an estimated cost of health care services, medication, and lost productivity from cardiovascular disease at approximately $312 Billion.

A lack of oxygenated blood to the myocardial tissue creates ischemia and is the most common condition presented in the clinic requiring treatment for heart disease. Currently, there are three treatments for CVD: 1) lifestyle change, 2) medications (optimal medical therapy) and 3) Interventional procedures and devices such as angioplasty and stenting, coronary artery bypass (CABG), and circulatory support devices.

The focus of interventional treatments has been on epicardial coronary arteries as a means to reestablish flow to ischemic tissue; the two most common procedures are percutaneous transluminal coronary angioplasty (PTCA), and CABG. These procedures can be limited by a number of complications such as abrupt vessel closure, restenosis, lesions that are totally occluded, and diffuse or long lesions that may not be "stentable."

Perhaps most significantly, occlusion of a coronary artery can cause detrimental changes to occur in the cardiac arterioles and capillaries that cause the so-called "no-reflow phenomenon" post CABG or PTCA. "No-reflow" may prevent adequate healing of ischemic tissue and inhibit development of collateral vasculature. Additionally, no-reflow is more pronounced in the sub-endocardium and becomes more common the longer the myocardium remains ischemic. Other anatomical anomalies, porcelain vessels, and lack of useful grafting tissue compound a myriad of problems that complicate "normal" coronary disease treatments.

An estimated 15% of the population presenting in the clinic are not suitable for CABG. For this so-called "no-option" patient population, mechanical circulatory support devices (VADs) or eventually heart transplant may be the only options.

It has long been proposed to deliver oxygenated arterial blood delivery through the coronary venous system 30, called retroperfusion, to the ischemic myocardium, with original proposals dating back to at least 1898, Pratt F H., The nutrition of the heart through the vessels of Thebesian and the coronary veins. Am J Physiol 1: 86-103, 1898, proposed the idea of perfusion of the heart muscle through the coronary sinus in isolated feline hearts. This work suggested that venous retroperfusion can provide some degree of nutritional delivery. In 1949, Beck C. Revascularization of the heart. Surgery 26: 82-88, 1949 described initial attempts of chronic retroperfusion of the coronary sinus by means of anastomosis to an arterial vessel [coronary venous bypass graft, (CVBG)]. In 1956, Lillehei C W, DeWall R A, Gott V L, Varco R L., The direct vision correction of calcification of calcific aortic stenosis by means of pump-oxygenator and retrograde coronary sinus perfusion. Dis Chest 30: 123-132, 1956 was the first to use this technique during cardiac surgery for myocardial protection.

Coronary retroperfusion was quickly abandoned, however, because of structural damage of the coronary sinus wall as well as intramyocardial vasculature produced by drainage disruption and elevated pressures (see Syeda B, Schukro C, Heinze G, Modaressi K, Glogar D, Maurer G, Mohl W. The salvage potential of coronary sinus interventions: meta-analysis and pathophysiologic consequences. J Thorac Cardiovasc Surg 127: 1703-1712, 2004.) Hemorrhage of the myocardium was reported as a complication during retroperfusion involving an arteriovenous shunt driven by an external roller pump through a catheter wedged in the anterior interventricular vein (See Zalewski A, Goldberg S, Slysh S, Maroko P R. Myocardial protection via coronary sinus interventions: superior effects of arterialization compared with intermittent occlusion. Circulation 71: 1215-1223, 1985). These complications, in conjunction with the adoption of coronary artery bypass grafting (CABG) and the eventual development of percutaneous transluminal coronary angioplasty (PTCA), limited the retroperfusion concept and coronary sinus interventions clinically.

At least two distinct pumpless approaches of coronary retroperfusion have been described relatively recently, both with arguable potential for chronic application: 1) percutaneous in situ coronary venous arterialization (PICVA) and 2) stent-based ventricle-to-vein bypass (venous VPASS).

PICVA is a catheter-based technique developed to provide arterial blood flow from the native coronary artery to the coronary vein while the outflow toward the coronary sinus is blocked (See Oesterle S N, Reifart N, Hauptmann E, Hayase M, Yeung A C. Percutaneous in situ coronary venous arterialization. Report of the first human catheter-based coronary artery bypass. Circulation 103: 2539-2543, 2001.) The major limitation of this approach is the procedural complexity, requiring penetration of the arterial wall to access the nearby vein, which is often difficult in no-option patients with significant diffuse disease. Furthermore, this method creates a sudden increase in coronary venous pressure and may be associated with subsequent myocardial hemorrhage.

The earlier VPASS approaches have included catheter-based approaches, which placed a stent based device designed to provide systolic blood flow directly from the left ventricle into either a coronary artery or a coronary vein. One limitation of this procedure as proposed is the necessity of selective catheterization of the veins draining the ischemic territory (See Raake P, Hinkell R, Kupatt C, von Brühl M L, Beller S, Andrees M, Vicol C, Boekstegers P. Percutaneous approach to a stent-based ventricle to coronary vein bypass (venous VPASS): comparison to catheter-based selective pressure-regulated retro-infusion of the coronary vein. Eur Heart J 26: 1228-1234, 2005). A more fundamental limitation is the inability of this approach as developed is to provide complete perfusion of the subendocardium during systole. Furthermore, the blood may be suctioned from the coronary venous system during diastole.

Thus there remains a great need in the art for a method and associated system to re-establish flow of oxygenated blood to tissue that has been starved due to stenosis or occlusion from emboli and may be positioned as an alternative or adjunct to PTCA, CABG, or mechanical circulatory support (VADs).

SUMMARY OF THE INVENTION

In accordance with one aspect of the present invention, the present invention, in summary, provides a method for stimulation of collateral development in ischemic cardiac regions comprising the fluid coupling of the left ventricle of the heart to the anterior interventricular vein to stimulate collateral development in ischemic regions via venous retroperfusion and operate at pressures to avoid damage to the venous vasculature.

The method for stimulation of collateral development in ischemic cardiac regions according to invention may provide wherein the fluid coupling of the left ventricle of the heart to the anterior interventricular vein includes a control of the diastolic/systolic pressure in the venous system to be within about 20-50 mmHg.

In accordance with one aspect of the present invention, the present invention, in summary, provides an apparatus for stimulation of collateral development in ischemic cardiac regions via the fluid coupling of the left ventricle of the heart to the anterior interventricular vein, said apparatus comprising: a transmyocardial conduit extending into the left ventricle of the heart; and a tri-directional coupler attached to the anterior interventricular vein and fluidly coupled to the transmyocardial conduit.

In accordance with one aspect of the present invention, the present invention, in summary, provides an apparatus for stimulation of collateral development in ischemic cardiac regions configured for fluid coupling of the left ventricle of the heart to the anterior interventricular vein to stimulate collateral development in ischemic regions, and wherein the fluid coupling of the left ventricle of the heart to the anterior interventricular vein is configured to control of the diastolic/systolic pressure in the venous system to be within about 20-50 mmHg.

The particular advantages of the present invention will be described in connection with the attached figures wherein like reference numerals represent like elements throughout.

BRIEF DESCRIPTION OF THE DRAWINGS

FIG. 1A is a schematic view of an apparatus for stimulation of collateral development in ischemic cardiac regions via venous retroperfusion through the fluid coupling of the left ventricle of the heart to the anterior interventricular vein in accordance with one embodiment of the invention;

FIG. 1B is an enlarged schematic view of a suture cuff portion of a transmyocardial conduit of the apparatus of FIG. 1A;

FIG. 1C is an enlarged schematic view of a tri-directional coupler for attachment to the anterior interventricular vein of the apparatus of FIG. 1A;

FIG. 2A is a schematic view of the normal physiology of the cardiac region of interest;

FIG. 2B is a schematic view of the physiology of the cardiac region of interest yielding ischemic cardiac regions;

DETAILED DESCRIPTION OF THE PREFERRED EMBODIMENTS

Figure 3B:
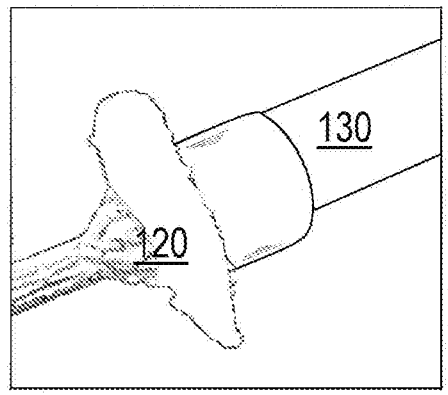
FIG. 3B is an enlarged schematic view of a suture cuff portion of the transmyocardial conduit of FIG. 3A.

It has been stated that if the coronary venous system consists of only epicardial drainage into the coronary sinus (i.e., single arterial inlet and single venous outlet), then retroperfusion will result in stagnation of flow and an increase in venous pressure to arterial levels. Coronary retroperfusion is possible, however, because the coronary venous anatomy extends beyond the coronary sinus 30. There exist many endo-thebesian vessels 24 with communications or interconnections within each system and in between the two systems FIG. 2A schematically illustrates the normal physiology of coronary circulation of the cardiac region of interest, while FIG. 2B is a schematic view of the physiology of coronary circulation of the cardiac region of interest yielding ischemic cardiac regions. The myocardium 10, generally defined as the middle and thickest layer of the heart wall, composed of cardiac muscle, represents the heart structure around the left ventricle 12 with the myocardium having an epicardial surface 16 and an endocardial surface 16. As well known the left ventricle 12 is the left lower chamber of the heart that receives blood from the left atrium and pumps it out under high pressure through the aorta to the body.

The "LAD" 24, or left anterior descending artery, or anterior interventricular branch of the left coronary artery, or anterior descending branch, is an artery of the heart passes at first behind the pulmonary artery and then comes forward between that vessel and the left auricula to reach the anterior interventricular sulcus, along which it descends to the incisura apicis cordis. Of note, because the LAD artery 24 provides much of the bloodflow for the left ventricle, which in turn provides much of the propulsive force for ejecting oxygenated blood to systemic circulation via the aorta, blockage of this artery is particularly associated with mortality. In the medical community ischemic heart attacks associated with this blood vessel are colloquially called "the Widowmaker." The LAD vein 28 leads to the coronary sinus 30 which is a collection of veins joined together to form this large vessel that collects blood from the myocardium 10. It delivers deoxygenated blood to the right atrium.

FIGS. 2A and B effectively illustrate a schematic of the coronary vasculature where the venous system has inter-venous connections, thebesian-sinus connections and a venous plexus. During coronary retroperfusion described below some flow proceeds through the capillaries and to the arterial tree or capillaries 18. Alternatively, the flow may also distribute through the venous plexus 22 and drain into the thebesian vessels 24, i.e., a second concurrent perfusion route. Finally, the flow may be shunted away via intervenous anastomosis 20 or sinus-Thebesian vessel 24 connections (and these can be identified as concurrent perfusion routes 3 and 4, respectively).

Figure 3C:
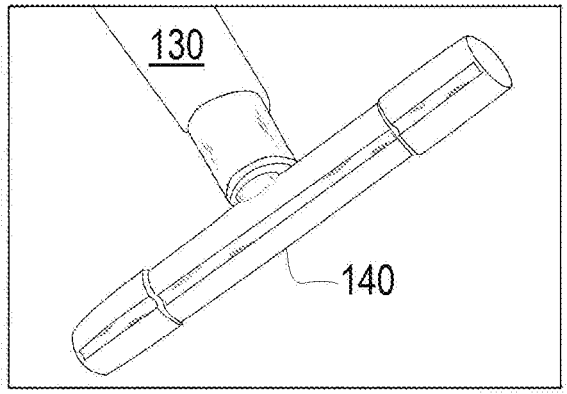
FIG. 3C is an enlarged schematic view of another tri-directional coupler for attachment to the anterior interventricular vein of the apparatus of FIG. 1A.
Figure 3A:
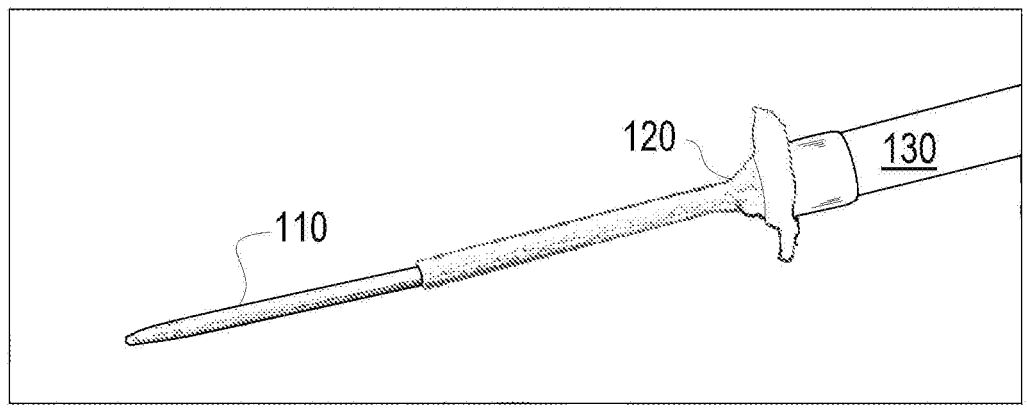
FIG. 3A is a schematic view of another transmyocardial conduit of the apparatus of FIG. 1A.

FIGS. 1A-C and 3A-C schematically illustrate an apparatus 100 that connects the left ventricle 12 (LV) of the heart to the anterior interventricular vein (AIV) 28 to stimulate collateral development in ischemic regions via venous retroperfusion of the disease free venous system of the heart. As alluded to above, venous retroperfusion has been demonstrated to create fluid shear stresses sufficient to achieve arteriogenesis. CABG and PTCA procedures attempt to reestablish flow to the ischemic myocardium using the disease compromised arterial vasculature of the heart. However, the extent of perfusion to the myocardium necessary for arteriogenesis is not necessarily achieved due to inability to perfuse ischemic areas from the arterial side. This condition is commonly called the "no reflow" phenomenon where the key distinction is that arterial flow does not necessarily equal perfusion to the capillary beds of the ischemic myocardium.

The proposed system and method of the present invention is comprised of a vascular connector apparatus (coupler 140) facilitating efficient placement in the AIV 28 and controlling the outlet pressure and a vascular conduit 110 that includes a balloon expandable stent or conduit 110 to achieve a left ventricle 12 trans-myocardial channel and a non-thrombogenic vascular graft 130 coupling the conduit 110 and the coupler 140. The apparatus 100 achieves the desired 20-50 mmHg outlet pressure from coupler 140 using a commercially available 3 mm stent (forming element 110) and 3 mm graft segment 130 through the design of tri-directional (T-shaped) AIV shaped connector 140. The LV-AIV venous reperfusion device or apparatus 100 of the invention is specifically designed to allow rapid, safe, and controlled perfusion of oxygenated blood from the LV 12 to the AIV 28. A key innovative aspect of the device 100 is that the device 100 is specifically designed to create a channel for the left ventricle to the AIV, and maintain a safe level of pressure and effective retroperfusion to the venous plexus in order to create global support to the myocardial tissue, especially ischemic tissue, and in the process create fluid shear forces that stimulate high level collateral development to repair ischemic myocardium.

Each component of the device 100 is designed to achieve the safe overall blood delivery pressure range of 20-50 mmHg. This device 100 demonstrates collateral development from non-ischemic regions via venous retroperfusion to the ischemic regions not being perfused from the arterial system of the heart. The proposed device 100 goes one step beyond traditional thinking of selective perfusion requiring ligation. The device 100 does not force retroperfusion distal by ligation, and promotes global retroperfusion of the venous plexus.

Transmyocardial LV Conduit 110 may be formed effectively from a commercially available PTFE-covered stent such as the Atrium ICAST™ stent, (Atrium, Hudson, N.H.). The collapsed diameter will be minimized but driven by the collapsed dimension of a 3 mm balloon catheter, such as the NC SPRINTER RX™ by MDT). Expanded diameter will be about 3 mm (+/−0.3 mm) over the expanded length. Stent length will be minimized, likely length: ≥24 mm, ≤28 mm, but driven by the anticipated LV wall thickness. The collapsed diameter of conduit 110 facilitates small introducer tools and the expanded diameter of conduit 110 facilitates adequate flow from LV 12.

A sewing or suture cuff 120 may be coupled to the conduit 110 to serve as a stop to control insertion of the conduit 110 and provide the clinician with a feature to suture against the epicardial surface 14.

The transmyocardial stent 110, as well as the graft subassembly 130 and the tri-directional AIV coupler 140 subcomponent, will be treated with a bioactive surface treatment prior to assembly. The preferred treatment is a covalently bonded heparin surface developed by the applicant Ension (known as an EBS™ treatment) and shown to be more bioactive and stable that other commercial similar bioactive surface treatments or coatings. This preferred process is detailed in Ension U.S. Pat. Nos. 8,114,465 and 8,157,818, which are incorporated herein by reference. The surface may be characterized by XPS (Analytical Answers, Woburn, Mass.) and bioactivity of this surface will be assessed using chromogenic assays to determine thrombin deactivation per $cm^2$ of surface area. Bioactivity of the treated surfaces will be about 0.8 IU IIa Deactivation/$cm^2$ as described in recent Ension publications.

The graft segment 130 may be effectively formed as a coil reinforced kink-resistant ePTFE 3 mm inner diameter vascular graft (such as sold under the ADVANTA SST™ from Atrium) with the EBS™ surface modification or treatment as discussed above. Graft segment 130 length will be minimized, namely less than 10 cm and preferably less than 7.5 cm, to reduce biomaterial blood exposure but driven by the venotomy junction placement and anticipated distance to conduit placement as discussed below. The 3 mm ID for graft segment 130 is suitable to achieve the pressure, flow, and shear stress functional specifications of a 20-50 mmHg based on 50-100 ml/min flow range.

The Tri-directional AIV Coupler 140 is formed as a custom tri-directional intravascular coupler. This custom formed coupler 140 is the primary functional component of the AIV junction and key to the control of the pressure within the safe 20-50 mmHg range for the anticipated 50-100 ml/min flow range at initiation.

The coupler 140 features a single 'graft-arm' coupled to segment 130 and two 'AIV-arms' coupled to the AIV 28. Inside diameter dimensions of arms will be driven primarily by the LV-AIV channel/apparatus 100 flow requirements, and outside diameter dimensions minimized for ease of AIV 28 venotomy insertion. However graft arm ID of about 3 mm and AIV arm ID of about 2.5 mm seem to be sufficient. The angle between graft-arm and the co-linear AIV-arms may be altered to optimize possible junction designs (such as through transient flow simulations (for one cardiac cycle) using a SOLIDWORKS® Flow Simulation). However, three discrete junction fluid body configurations, namely graft-arm/AIV-arm angles of 45 (FIG. 1), 60 (not shown) and 90° (FIG. 3), are anticipated with the present invention. The total length of AIV coupler is 3 cm, however the length of AIV arms and angle of graft arm will be driven by clinician preference to facilitate ease of venotomy insertion of arms of the coupler 140 into AIV 28.

The fabrication of the device 100 may be as follows. A commercially available balloon expandable covered 3 mm ID (expanded) stent which forms the primary aspect of the conduit 110, such as the ICAST™ brand from Atrium may be modified with a flaring tool to achieve a proximal flared dilation to the 3 mm expanded diameter. The proximal flared end of the conduit 110 will be mechanically coupled to one end of a reinforced 3 mm ID ePTFE vascular graft that forms the segment 130, such as sold under the ADVANTA SST™ by Atrium) using a crimped connection (shown in small left image of FIG. 1). A DACRON® ring (6 mm ID and 12 mm OD) may be cut to form the reinforced sewing cuff 120. The interface between the stent and graft, along with the Dacron ring will be cast within the sewing cuff 120 using a mold and Dow MDX4-4210 medical grade adhesive silicone. The thus formed mesh-reinforced sewing cuff 120 will serve as a "stop" to control insertion of the conduit 110 into the myocardium 12 and provide the clinician with a feature to suture against the epicardium for additional security and conformal profile on the epicardium.

While various sized anastomotic couplers 140 may ultimately be appropriate to accommodate AIVs of varying sizes in clinical use, the preferred embodiment of device 100 provides 2.5 mm ID AIV-arms to accommodate the anticipated AIV size in implementation. More generally the ID of vascular arms will be custom sized to affect a pressure drop to deliver blood at the 20-50 mmHg pressure range demonstrated as safe for the venous system. The input arm will be 3 mm ID and thin-walled to accommodate a stretched fit of the vascular graft portion 130 with smooth flow transition. The AIV coupler 140 may be fabricated from solid titanium (6AL-4V) rod stock which can facilitate 4-axis CNC mill fabrication of the coupler 140. Titanium also accommodates a thin wall design, machine fabrication, and known compatibility with the EBS surface treatment. The coupler 140 fabrication will affect smooth inner surfaces and bumps/grooves on outer surfaces of AIV-arms to accommodate circumferential securing with sutures following venotomy insertion. The graft-arm of the coupler 140 will feature a bump to accommodate a crimped ferrule bond with the vascular graft segment 130 through a ferrule that may be machined from 316 stainless steel tubing. The free end of the vascular graft segment 130 will be fed through the ferrule and then placed over the graft-arm of the AIV coupler 140. The ferrule will then be positioned over the graft-arm and crimped in place resulting in the completed assembly as illustrated in FIGS. 1 and 3. The final apparatus 100 will be placed in sterilization pouches, labeled, and sterilized such as by using low temperature ethylene oxide (EtO).

Ancillary components include an introducer, guide wire, a balloon catheter, and a balloon expander tool (such as a CORDIS OPTA PRO PTA™ dilation catheter) comprising the delivery system for the venous retroperfusion device of apparatus 100.

A summary of the implantation procedure is provided here. The transmyocardial conduit 110 is first placed through the myocardial into the left ventricle 12. An 18-gauge angiocath needle may be used to puncture the myocardium 10 into the LV 12. Communication with the left ventricle 12 is verified by flow through the needle. A guide wire, e.g., a nitinol wire, will be advanced through the angiocath and into the LV 12. After the needle is withdrawn, the venous reperfusion system (device 100 and deployment balloon) is advanced into place until the sewing cuff 120 is adjacent the epicardial surface 14. After placement is visually confirmed, the balloon catheter is expanded to form the transmyocardial channel through conduit 110. The balloon is temporarily deflated and channel formation is verified by blood flow from systolic contraction of the LV. The balloon may be re-inflated to assure channel uniformity at the expanded diameter of 3 mm. The expanded conduit 110 is effectively secured with in the myocardium 10. The balloon is deflated, and withdrawn from the lumen of the conduit 110 and the ePTFE graft segment 130 quickly cross-clamped. The clinician may then place suture from the sewing cuff 120 to the epicardial surface to secure placement. In one operational embodiment the free end of the vascular graft segment 130 may now be connected to the tri-directional coupler 140 via the crimped ferrule. A venotomy in the AIV 28 is constructed using customary procedures and, after loosening of the cross clamp to de-air the device, the co-linear AIV arms of the tri-directional AIV conduit 40 is placed in the AIV and secured in place using suture. After placement is confirmed, the cross clamp is removed to establish venous retroperfusion from the LV 12. In operation, inlet (LV) pressure range is 10-140 mmHg at the inlet of the conduit 110 and the outlet (AIV) pressure range: 20-50 mmHg at the outlet of the coupler 140. The LV pressure waveform will vary pressure over each cardiac cycle. The time needed to promote angiogenesis may be only a few weeks and thus the operation of the implanted device 100 need not be permanent. The operational pressures are at implantation and several months later may be lower. The patency of the device need only be for a period time sufficient to promote angiogenesis.

Although the present invention has been described with particularity herein, the scope of the present invention is not limited to the specific embodiment disclosed. It will be apparent to those of ordinary skill in the art that various modifications may be made to the present invention without departing from the spirit and scope thereof.

What is claimed is:

1. An apparatus (100) for stimulation of collateral development in ischemic cardiac regions comprising:
   a vascular tri-directional coupler (140) configured for placement in the anterior interventricular vein (28) including two co-linear arms with an inner diameter and co-linear openings at the ends thereof and a graft arm with an inner diameter connected to the co-linear arms;
   a transmyocardial conduit (110) which is configured to be inserted into the left ventricle (12) of the heart;
   a non-thrombogenic vascular graft (130) coupling the conduit (110) and the graft arm of the coupler (140) whereby the apparatus (100) provides for fluid coupling of the left ventricle (12) of the heart to the anterior interventricular vein (28) through the conduit (110) the graft (130) and the coupler (140) to stimulate collateral development in ischemic regions and wherein the conduit (100), coupler (140) and graft (130) are configured to achieve an overall blood delivery pressure range of 20-50 mmHg to avoid damage to the venous vasculature.

2. The apparatus (100) for stimulation of collateral development in ischemic cardiac regions according to claim 1, wherein the transmyocardial conduit (110) is configured to be inserted in a collapsed state and configured to be expanded after in position extending into the left ventricle (12) of the heart via venous retroperfusion.

3. The apparatus (100) for stimulation of collateral development in ischemic cardiac regions according to claim 2 wherein the transmyocardial conduit (110) has an expanded inner diameter of about 2-4 mm.

4. The apparatus (100) for stimulation of collateral development in ischemic cardiac regions according to claim 1, wherein the tri-directional coupler (140) has an inner diameter of each of the arms of about 2-4 mm.

5. The apparatus (100) for stimulation of collateral development in ischemic cardiac regions according to claim 1, wherein the coupling conduit (130) extends for less than 10 cm between the transmyocardial conduit (110) and the tri-directional coupler (140).

6. The apparatus (100) for stimulation of collateral development in ischemic cardiac regions according to claim 1, further including a suture cuff (120) on the transmyocardial conduit (110).

\* \* \* \* \*